(12) United States Patent
Terui et al.

(10) Patent No.: US 10,441,238 B2
(45) Date of Patent: Oct. 15, 2019

(54) RADIATION IMAGING APPARATUS, CONTROL METHOD THEREOF, AND PROGRAM

(71) Applicant: CANON KABUSHIKI KAISHA, Tokyo (JP)

(72) Inventors: Kosuke Terui, Yokohama (JP); Atsushi Iwashita, Tokyo (JP); Katsuro Takenaka, Honjo (JP); Shinichi Takeda, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 211 days.

(21) Appl. No.: 15/563,148

(22) PCT Filed: Jun. 3, 2016

(86) PCT No.: PCT/JP2016/002697
§ 371 (c)(1),
(2) Date: Sep. 29, 2017

(87) PCT Pub. No.: WO2017/006513
PCT Pub. Date: Jan. 12, 2017

(65) Prior Publication Data
US 2018/0070906 A1  Mar. 15, 2018

(30) Foreign Application Priority Data
Jul. 8, 2015 (JP) .................................. 2015-137225

(51) Int. Cl.
*A61B 6/00* (2006.01)
*H04N 5/357* (2011.01)
(Continued)

(52) U.S. Cl.
CPC ................ *A61B 6/54* (2013.01); *A61B 6/482* (2013.01); *A61B 6/5258* (2013.01);
(Continued)

(58) Field of Classification Search
CPC ....................................................... H04N 5/357
See application file for complete search history.

(56) References Cited

U.S. PATENT DOCUMENTS

| 5,144,141 A | 9/1992 | Rougeot et al. .............. 250/369 |
| 7,256,404 B2 | 8/2007 | Inoue et al. |
| (Continued) | | |

FOREIGN PATENT DOCUMENTS

| JP | H01-265184 | 10/1989 |
| JP | H10-221455 | 8/1998 |
| (Continued) | | |

OTHER PUBLICATIONS

Translation of JP 2001-194460 (Year: 2001).*
(Continued)

*Primary Examiner* — Yara B Green
(74) *Attorney, Agent, or Firm* — Venable LLP (57) ABSTRACT

A radiation imaging apparatus is provided. The apparatus comprises a scintillator configured to convert radiation into light, a sensor panel in which a plurality of pixels each comprising a light detector configured to detect the light is arranged, and a processing unit. The processing unit comprises a conversion unit configured to output a detection signal in accordance with a signal generated in the light detector by the incident light and radiation that has transmitted through the scintillator without being converted into light, and a reset control unit configured to determine that the light detector detects the transmitted radiation based on a magnitude of the detection signal and reset the conversion unit if the light detector is determined to detect the transmitted radiation.

15 Claims, 10 Drawing Sheets

(51) Int. Cl.
   *H04N 5/32*     (2006.01)
   *G06T 11/00*    (2006.01)
   *G01T 1/20*     (2006.01)

(52) U.S. Cl.
   CPC ............. *G06T 11/005* (2013.01); *H04N 5/32* (2013.01); *H04N 5/357* (2013.01); *G01T 1/20* (2013.01)

(56) References Cited

U.S. PATENT DOCUMENTS

| | | | |
|---|---|---|---|
| 7,342,221 B2 | 3/2008 | Takenaka et al. | |
| 7,343,000 B2 | 3/2008 | Kameshima et al. | |
| 7,381,963 B2 | 6/2008 | Endo et al. | |
| 7,386,089 B2 | 6/2008 | Endo et al. | |
| 7,391,029 B2 | 6/2008 | Takeda et al. | |
| 7,403,594 B2 | 7/2008 | Endo et al. | |
| 7,442,939 B2 | 10/2008 | Yagi et al. | |
| 7,491,960 B2 | 2/2009 | Takenaka et al. | |
| 7,514,663 B2 | 4/2009 | Yagi et al. | |
| 7,514,686 B2 | 4/2009 | Ogawa et al. | |
| 7,514,690 B2 | 4/2009 | Endo et al. | |
| 7,532,706 B2 | 5/2009 | Kameshima et al. | |
| 7,541,591 B2 | 6/2009 | Endo et al. | |
| 7,573,038 B2 | 8/2009 | Yokoyama et al. | |
| 7,573,041 B2 | 8/2009 | Kameshima et al. | |
| 7,595,493 B2 | 9/2009 | Okada et al. | |
| 7,613,277 B2 | 11/2009 | Takenaka et al. | |
| 7,714,294 B2 | 5/2010 | Sawada et al. | |
| 7,718,973 B2 | 5/2010 | Endo et al. | |
| 7,723,693 B2 | 5/2010 | Okada et al. | |
| 7,724,874 B2 | 5/2010 | Kameshima et al. | |
| 7,732,776 B2 | 6/2010 | Takenaka et al. | |
| 7,732,778 B2 | 6/2010 | Yokoyama et al. | |
| 7,750,309 B2 | 7/2010 | Endo et al. | |
| 7,777,167 B2 | 8/2010 | Takeda et al. | |
| 7,791,035 B2 | 9/2010 | Yokoyama et al. | |
| 7,847,263 B2 | 12/2010 | Yagi et al. | |
| 7,850,367 B2 | 12/2010 | Takenaka et al. | |
| 7,869,568 B2 | 1/2011 | Yokoyama et al. | |
| 7,880,145 B2 | 2/2011 | Yagi et al. | |
| 7,952,058 B2 | 5/2011 | Nomura et al. | |
| 8,107,588 B2 | 1/2012 | Kameshima et al. | |
| 8,115,177 B2 | 2/2012 | Takeda et al. | |
| 8,222,611 B2 | 7/2012 | Yagi et al. | |
| 8,247,779 B2 | 8/2012 | Kameshima et al. | |
| 8,304,735 B2 | 11/2012 | Inoue et al. | |
| 8,440,975 B2 | 5/2013 | Inoue et al. | |
| 8,502,155 B2 | 8/2013 | Ballabriga et al. | ...... 250/370.08 |
| 8,576,294 B2 | 11/2013 | Kameshima et al. | |
| 8,653,463 B2 | 2/2014 | Sawada et al. | |
| 8,723,996 B2 | 5/2014 | Yokoyama et al. | |
| 8,792,024 B2 | 7/2014 | Takenaka et al. | |
| 8,809,795 B2 | 8/2014 | Takenaka et al. | |
| 8,829,438 B2 | 9/2014 | Sato et al. | |
| 9,048,154 B2 | 6/2015 | Takenaka et al. | |
| 9,081,104 B2 | 7/2015 | Sawada et al. | |
| 9,128,196 B2 | 9/2015 | Sato et al. | |
| 9,134,432 B2 | 9/2015 | Iwashita et al. | |
| 9,234,966 B2 | 1/2016 | Sugawara et al. | |
| 9,354,333 B2 | 5/2016 | Inoue et al. | |
| 9,366,767 B2 | 6/2016 | Inoue et al. | |
| 9,423,512 B2 | 8/2016 | Sato et al. | |
| 9,445,030 B2 | 9/2016 | Yagi et al. | |
| 9,462,989 B2 | 10/2016 | Takenaka et al. | |
| 9,468,414 B2 | 10/2016 | Ryu et al. | |
| 9,470,800 B2 | 10/2016 | Iwashita et al. | |
| 9,470,802 B2 | 10/2016 | Okada et al. | |
| 9,541,653 B2 | 1/2017 | Iwashita et al. | |
| 9,655,586 B2 | 5/2017 | Yagi et al. | |
| 9,737,271 B2 | 8/2017 | Iwashita et al. | |
| 9,812,474 B2 | 11/2017 | Yagi et al. | |
| 2010/0020922 A1* | 1/2010 | Carmi ................... G01T 1/1644 378/19 |
| 2010/0148080 A1 | 6/2010 | Endo et al. | |
| 2010/0187432 A1 | 7/2010 | Herrmann et al. | ........... 250/395 |
| 2011/0317054 A1 | 12/2011 | Kameshima et al. | |
| 2013/0187054 A1 | 7/2013 | Ishii et al. | |
| 2013/0221198 A1 | 8/2013 | Sawada et al. | |
| 2014/0034836 A1 | 2/2014 | Takei et al. | |
| 2014/0112448 A1 | 4/2014 | Takenaka et al. | |
| 2014/0239186 A1 | 8/2014 | Sato et al. | |
| 2014/0285689 A1 | 9/2014 | Ryu et al. | ..................... 348/421 |
| 2014/0361189 A1 | 12/2014 | Kameshima et al. | |
| 2016/0084969 A1 | 3/2016 | Sato et al. | |
| 2016/0178764 A1 | 6/2016 | Ryu et al. | |
| 2016/0270755 A1 | 9/2016 | Takenaka et al. | |
| 2017/0285189 A1 | 10/2017 | Ryu et al. | |

FOREIGN PATENT DOCUMENTS

| | | |
|---|---|---|
| JP | 2001-194460 | 7/2001 |
| JP | 2001-228252 | 8/2001 |
| JP | 2013-501226 | 1/2013 |

OTHER PUBLICATIONS

U.S. Appl. No. 15/564,946, Kosuke Terui, filed Oct. 6, 2017.
U.S. Appl. No. 15/791,566, Atsushi Iwashita, filed Oct. 24, 2017.

* cited by examiner

RADIATION IMAGING APPARATUS, CONTROL METHOD THEREOF, AND PROGRAM

TECHNICAL FIELD

The present invention relates to a radiation imaging apparatus, a control method thereof, and a program.

BACKGROUND ART

There is known a radiation imaging apparatus that uses, as an imaging apparatus used for medical imaging diagnosis or non-destructive inspection by radiation, a flat panel detector (to be referred to as FPD hereinafter) formed from a semiconductor material. Such a radiation imaging apparatus can be used, for example, in medical imaging diagnosis, as a digital imaging apparatus for obtaining a still image or a moving image.

An integral sensor and a photon counting sensor are available as a radiation detection method used for FPDs. An integral sensor measures the total amount of charges generated from incident radiation. Meanwhile, a photon counting sensor identifies the energy (wavelength) of incident radiation and obtains the detection count of radiation for each energy level. That is, since the photon counting sensor has an energy resolution, the diagnosis capability can be improved compared to the integral sensor.

Japanese Patent Laid-Open No. 2013-501226 proposes a direct type photo counting sensor that directly detects radiation in each pixel by using CdTe. In addition, Japanese Patent Laid-Open No. 2001-194460 proposes an indirect type photo counting sensor that converts incident radiation into light by a scintillator and detects the light converted from the radiation in each pixel.

SUMMARY OF INVENTION

Single crystal CdTe used in a direct type sensor can only grow to about a few cm square. Therefore, it is difficult and very costly to increase the area of a direct type sensor. Although there is a method of implementing a direct type sensor with a large area by depositing amorphous Se, a sensor manufactured by this method operates slowly and requires temperature management.

Meanwhile, an indirect type sensor is advantageous since it is easy to increase the area and low in cost. However, a sensor that detects light converted by a scintillator has sensitivity not only to light but also to radiation, and thus may detect some radiation rays that have transmitted through the scintillator. Signal charges generated if a light detector of a sensor directly detects radiation is about ten times larger in amount than signal charges generated if the light detector detects the light converted by the scintillator. If radiation enters directly, the amount of the signal charges generated in the light detector is large, increasing a signal amplitude output from a conversion circuit that receives the signal charges and converts them into a voltage signal. Since the signal amplitude is large, a fall time until the voltage signal of the conversion circuit returns to an initial value becomes longer. If the light detector detects light during a fall time of a large signal amplitude, the voltage signal received from the light detector and converted by the conversion circuit may be buried in the large signal amplitude. If the signal is buried, the sensor cannot detect light or may erroneously determine energy of radiation. This may cause poor image quality of a captured image.

Japanese Patent Laid-Open No. 2001-194460 discloses a technique of discriminating between a signal that detects radiation directly based on the magnitude of a signal amplitude and a signal that detects light converted by a scintillator. However, Japanese Patent Laid-Open No. 2001-194460 does not disclose a possibility that a generated signal is influenced by a signal having a large signal amplitude when the light detector detects light during a fall period of the signal that has the large signal amplitude and detects radiation.

Some embodiments of the present invention provide a technique advantageous in suppressing the influence of a signal generated by direct incident radiation and improving image quality of a captured image in an indirect type photon counting sensor.

According to some embodiments, a radiation imaging apparatus comprising: a scintillator configured to convert radiation into light; a sensor panel in which a plurality of pixels each comprising a light detector configured to detect the light is arranged; and a processing unit, wherein the processing unit comprises: a conversion unit configured to output a detection signal in accordance with a signal generated in the light detector by the incident light and radiation that has transmitted through the scintillator without being converted into light; and a reset control unit configured to determine that the light detector detects the transmitted radiation based on a magnitude of the detection signal and reset the conversion unit if the light detector is determined to detect the transmitted radiation, is provided.

According to some other embodiments, a control method of a radiation imaging apparatus that comprises a scintillator configured to convert radiation into light and a sensor panel in which a plurality of pixels each comprising a light detector configured to detect the light is arranged, the method comprising: outputting a detection signal in accordance with a signal generated in the light detector by the incident light and radiation that has transmitted through the scintillator without being converted into light; determining that the light detector detects the transmitted radiation based on a comparison result between the detection signal and a predetermined reference; and resetting the detection signal if the light detector is determined to detect the transmitted radiation, is provided.

Further features of the present invention will become apparent from the following description of exemplary embodiments (with reference to the attached drawings).

DESCRIPTION OF EMBODIMENTS

Detailed embodiments of a radiation imaging apparatus according to the present invention will be described below with reference to the accompanying drawings. Note that in the following description and drawings, common reference numerals denote common components throughout a plurality of drawings. Hence, the common components will be described by cross-referring to the plurality of drawings, and a description of components denoted by common reference numerals will appropriately be omitted. Note that radiation according to the present invention can include not only α-rays, β-rays, and γ-rays that are beams generated by particles (including photons) emitted by radioactive decay but also beams having energy equal to or higher than the energy of these beams, for example, X-rays, particle beams, and cosmic rays.

Figure 1:
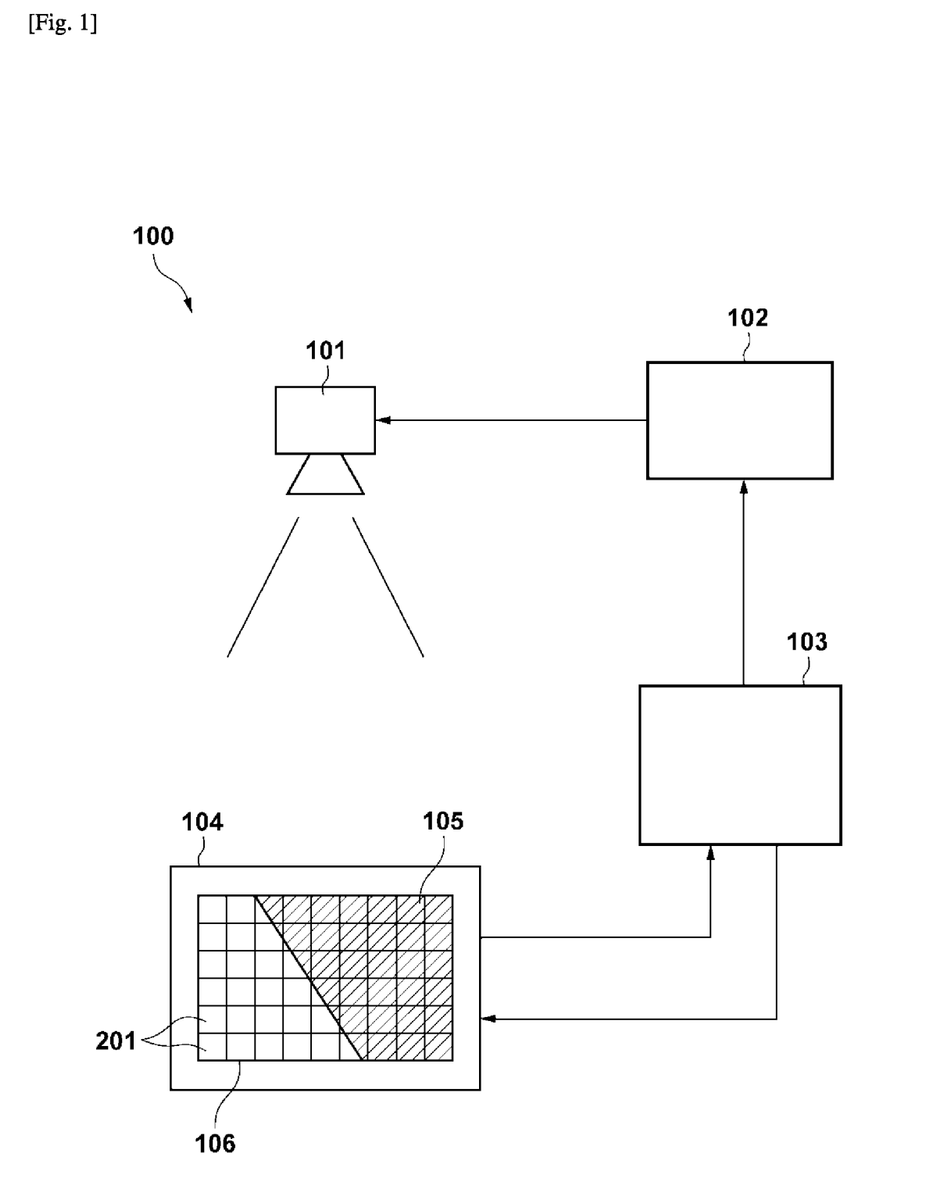
FIG. 1 is a block diagram showing an example of the arrangement of a radiation imaging apparatus according to the present invention.

A radiation imaging apparatus 100 (also referred to as a "radiation imaging system") according to a first embodiment of the present invention will be described. FIG. 1 shows an example of the arrangement of the radiation imaging apparatus 100 according to this embodiment. The radiation imaging apparatus 100 includes, for example, an irradiating unit 101 that irradiates an object with radiation, an irradiation control unit 102 that controls the irradiating unit 101, an imaging unit 104 for imaging the object irradiated with radiation, and a processor 103. Each of the irradiation control unit 102 and the processor 103 can be formed by, for example, a computer which includes a CPU, a memory, and the like. Although the irradiation control unit 102 and the processor 103 are formed separately in this embodiment, the present invention is not limited to this, and they may be formed integrally. That is, the irradiation control unit 102 and the processor 103 can be formed by one computer including these functions.

The imaging unit 104 includes, for example, a scintillator 105 that converts incident radiation into light and a sensor panel 106. In the sensor panel 106, for example, a plurality of pixels 201 each detecting light converted from radiation by the scintillator 105 are arranged so as to form a plurality of rows and a plurality of columns. Each pixel 201 (to be described in detail later) has an arrangement for performing photon counting radiation imaging and counts the number of photons of incident radiation based on each light detection result.

The processor 103 exchanges a signal or data with the imaging unit 104. More specifically, the processor 103 controls the imaging unit 104 to perform radiation imaging and receives a signal obtained by the operation from the imaging unit 104. The signal includes counted values of radiation photons. For example, the processor 103 generates, based on the counted values, image data for displaying a captured image by radiation on a display unit (not shown) such as a display or the like. In this case, the processor 103 can perform predetermined correction processing on the image data. In addition, the processor 103 supplies, to the irradiation control unit 102, a signal to start or end radiation irradiation.

Figure 2:
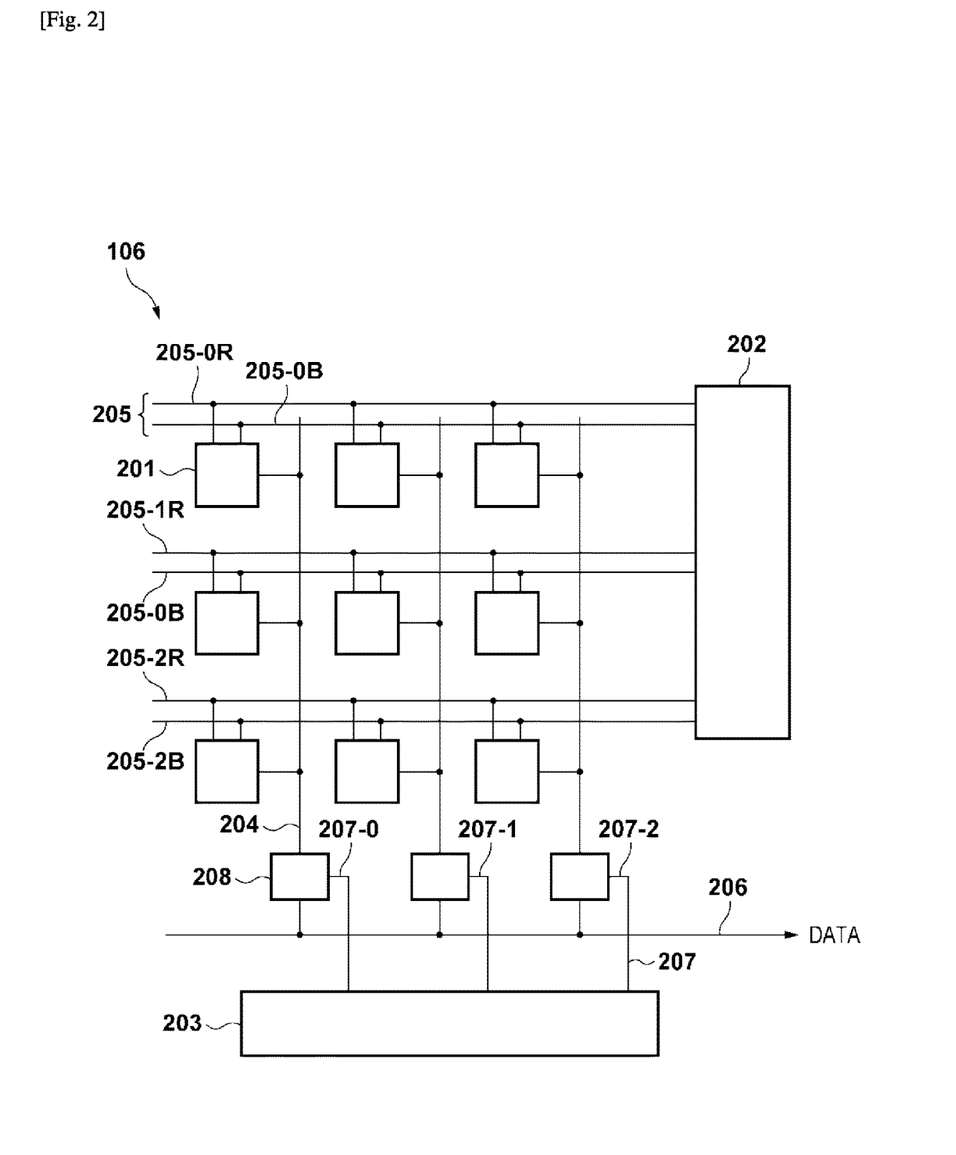
FIG. 2 is a block diagram showing the arrangement of a sensor panel of the radiation imaging apparatus in FIG. 1.

Next, the arrangement of the sensor panel 106 will be described with reference to FIG. 2. FIG. 2 is a block diagram showing the arrangement of the sensor panel 106. The sensor panel 106 may include, for example, the plurality of pixels 201, a vertical scanning circuit 202, a horizontal scanning circuit 203, column signal lines 204, signal lines 205, an output line 206, signal lines 207, and column selection circuits 208. Each of the plurality of pixels 201 may be configured to obtain the detection count of light generated in the scintillator 105 for each of a plurality of levels related to a light intensity. When a signal is supplied to each pixel 201 via the corresponding signal line 205, selected detection count data is output from each pixel 201 to the corresponding column selection circuit 208 via the corresponding column signal line 204.

The vertical scanning circuit 202 sequentially switches the signal lines 205 which supply signals so that the detection count data will be output from each pixel 201. If a signal is supplied to each column selection circuit 208 via the corresponding signal line 207, the detection count data output from each corresponding pixel 201 is output as data DATA to the output line 206. In addition, the horizontal scanning circuit 203 sequentially switches the signal lines 207 which supply signals so that the operation to output the detection count data to the output line 206 will be sequentially performed by the plurality of column selection circuits 208. Although the sensor panel 106 arranged with 3 rows×3 columns of pixels 201 has been shown for the sake of descriptive convenience in FIG. 2, a sensor panel 106 arranged with a larger number of pixels 201 can be used as well. For example, in a 17 inch sensor panel 106 (FPD), approximately 2,800 rows×2,800 columns of pixels 201 can be arranged in a two-dimensional array.

Figure 3:
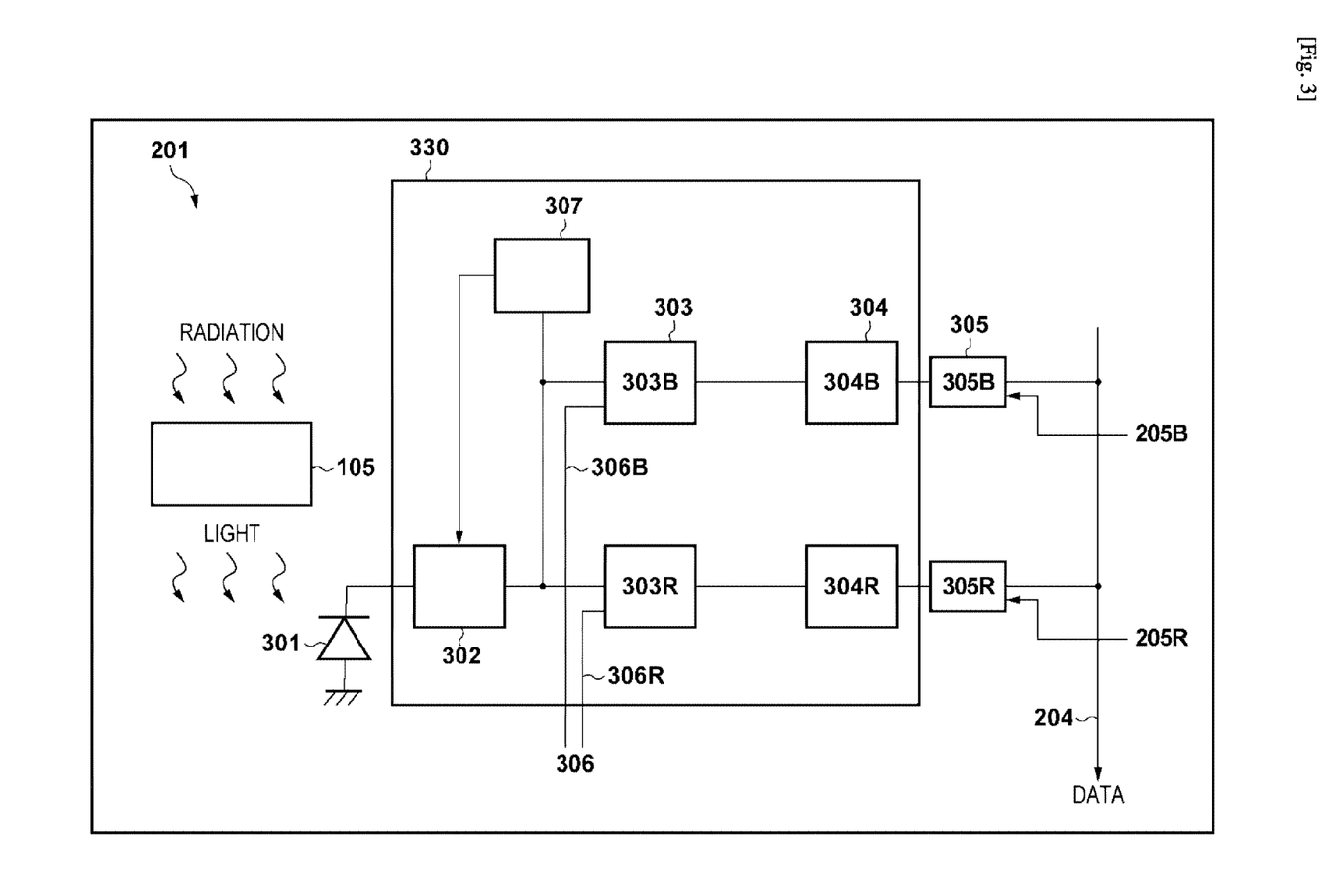
FIG. 3 is a block diagram showing the arrangement of a pixel of the radiation imaging apparatus in FIG. 1.

The arrangement of each pixel 201 will be described next with reference to FIG. 3. FIG. 3 is a block diagram showing the arrangement of the pixel 201. Each pixel 201 of the sensor panel 106 can include, for example, a light detector 301, a processing unit 330, output units 305, and a reference voltage unit that supplies reference voltages 306. The processing unit 330 can also include a conversion unit 302, comparison units 303, count units 304, and a reset control unit 307. The light detector 301 is a photoelectric converter that generates a signal by detecting light generated in the scintillator 105 when the radiation enters the scintillator 105. A known photoelectric conversion element such as a photodiode or the like can be used as the light detector 301. For example, a differential circuit is used as the conversion unit 302. The conversion unit 302 converts charges as the signal generated by the light detector 301 using, for example, the photodiode into a voltage signal as a detection signal and outputs the converted voltage signal to each comparison unit 303 and the reset control unit 307. The radiation imaging apparatus 100 generates a captured image based on the output count of this detection signal. More specifically, each comparison unit 303 compares the voltage of the voltage signal output from the conversion unit 302 with the corresponding reference voltage 306 and generates, for example, a binary signal as a comparison result signal in accordance with the comparison result. For example, if the light detector 301 detects light and the voltage of the voltage signal output from the conversion unit 302 is equal to or more than the voltage of each reference voltage 306, the corresponding comparison unit 303 outputs a digital value "1" as the signal in accordance with the comparison result. Meanwhile, if the voltage of the voltage signal output from the conversion unit 302 is less than each reference voltage 306, the corresponding comparison unit 303 outputs a digital value "0" as the signal in accordance with the comparison result. Each reference voltage 306 which is supplied to the corresponding comparison unit 303 may be set to be a common value for all of the pixels 201 in the sensor panel 106. Each count unit 304 obtains and stores the detection count of light by the light detector 301 and the output count of the digital value "1" out of the comparison result signal. If radiation enters the scintillator 105 and is converted into light, each comparison unit 303 generates a binary digital value signal, via the conversion unit 302, in accordance with the light detected by the light detector 301. Each count unit 304 stores the output count of the digital value "1" out of this signal. When the signal is supplied from the vertical scanning circuit 202 via each signal line 205 connected to the corresponding output unit 305, the output unit 305 supplies detection count data DATA stored in the corresponding count unit 304 to the corresponding column selection circuit 208 via the column signal line 204. Subsequently, when a signal is supplied to each column selection circuit 208 via the corresponding signal line 207, data DATA is output to the processor 103. The processor 103 generates image data.

In the arrangement shown in FIG. 3, two comparison units 303B and 303R are arranged in each pixel 201, and reference voltages 306B and 306R having different values are supplied to the respective comparison units 303B and 303R. Respective count units 304B and 304R are arranged at the subsequent stages of the respective comparison units 303B and 303R. Each pixel 201 can obtain and store the detection count of signals having different light intensities by the plurality of comparison units 303, reference voltages 306, and count units 304. The number of comparison units 303 is not limited to two, but may be one or three or more. For example, if the numbers of comparison units 303 and the reference voltages 306 are increased, a tone with respect to light intensity to be detected can be increased. Also, the number of count units 304 may be one or three or more. For example, the number of memories may be increased/decreased in accordance with the number of comparison units 303. Alternatively, for example, one count unit 304 may obtain and store together the respective detection counts in accordance with a plurality of light intensities.

The reset control unit 307 determines, from the voltage signal received from the conversion unit 302, whether the light detector 301 detects light converted from radiation by the scintillator 105 or whether the light detector 301 directly detects radiation that has transmitted through the scintillator 105. If the reset control unit 307 determines that the light detector 301 detects the radiation that has transmitted through the scintillator 105, it resets the conversion unit 302 immediately. For example, a signal is output only if the reset control unit 307 determines that the light detector 301 detects the radiation that has transmitted through the scintillator 105. This signal is input to the reset terminal of the conversion unit 302.

Figure 4A:
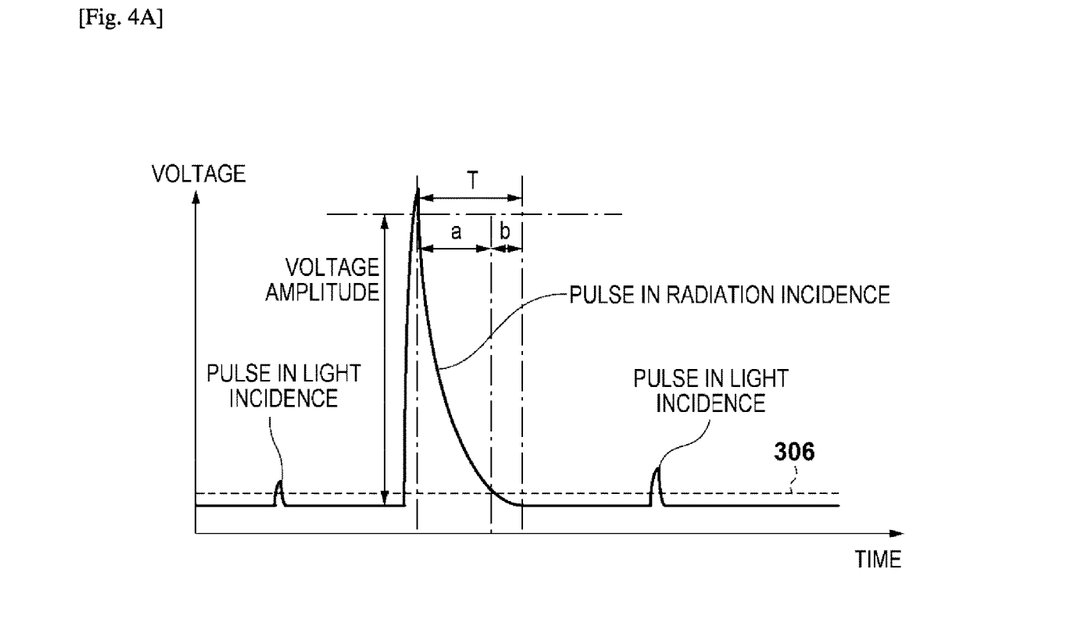
FIG. 4A is a graph showing an output waveform of a signal generating unit of the radiation imaging apparatus in FIG. 1.
Figure 4B:
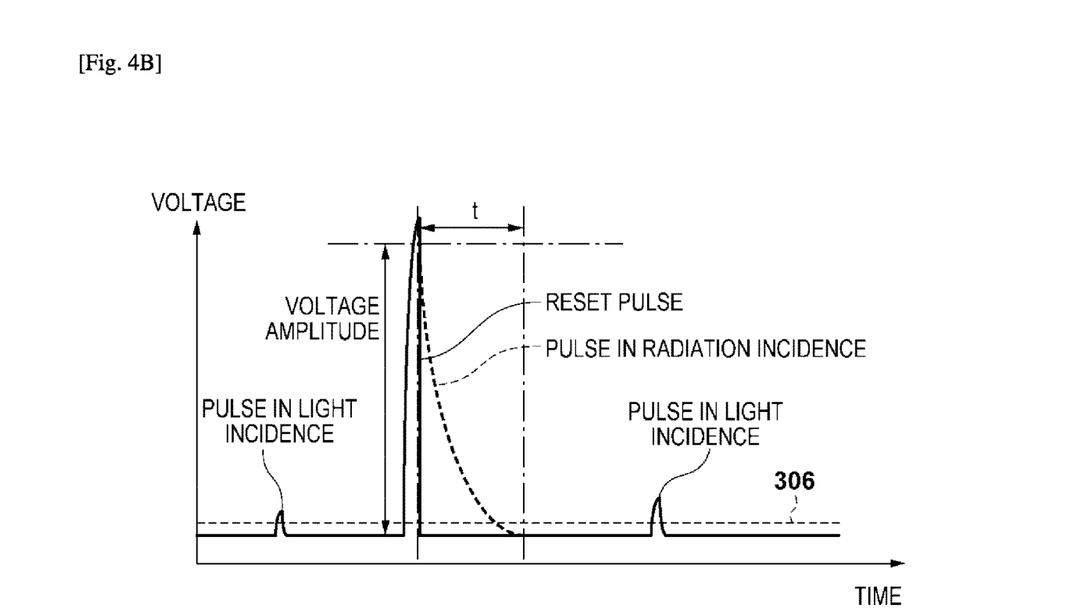
FIG. 4B is a graph showing an output waveform of a signal generating unit of the radiation imaging apparatus in FIG. 1.

FIG. 4A shows the waveform of the voltage signal output from the conversion unit 302. The waveform of FIG. 4A shows a voltage change of the voltage signal if the light converted from the radiation and the radiation that has transmitted through the scintillator 105 enter the light detector 301 with respect to the abscissa representing a time and the ordinate representing a voltage. For example, the amount of charges generated if the light detector 301 using the photodiode detects radiation is about ten times larger than the amount of charges generated if the light detector 301 detects light converted by the scintillator 105. Accordingly, a voltage obtained when radiation output from the conversion unit 302 that converts the signal generated in the light detector 301 into the voltage signal enters directly is higher than a voltage obtained when light enters and the amplitude of the voltage signal becomes larger. For example, the voltage obtained when the radiation enters directly indicates a voltage about ten times higher than the voltage obtained when the light enters. Therefore, a fall time until the voltage of the voltage signal returns to an initial state becomes longer. During a period a out of a fall time T when the voltage of the voltage signal generated by radiation exceeds each reference voltage 306, if light is detected by the light detector 301 and converted into a voltage signal, this voltage signal is buried in a voltage signal generated by incident radiation. It is therefore difficult to detect, by the comparison units 303, the light converted from the incident radiation during the period a. During a period b out of the fall time T when the voltage of the voltage signal falls below each reference voltage 306, if light is detected by the light detector 301 and converted into a voltage signal, a voltage of this voltage signal and a voltage obtained by radiation during the fall are superimposed on one another. Therefore, each comparison unit 303 may determine a value of a voltage signal generated by subsequent incident light to be higher than an actual value. It is therefore difficult to determine the count or energy of radiation that has entered during the fall time T. Accordingly, in this embodiment, if the reset control unit 307 determines that the light detector 301 detects the radiation that has transmitted through the scintillator 105, it resets the conversion unit 302 immediately. Upon resetting the conversion unit 302, a voltage signal generated by incident radiation is reset as shown in FIG. 4B and an output voltage returns to an initial value. Therefore, as compared to a case without reset, counting and energy determination can be performed on a voltage signal generated by light converted from radiation that has entered during a period t after resetting.

The reset control unit 307 detects the transmitted radiation based on the magnitude of the voltage signal received from the conversion unit 302. A method of detecting the transmitted radiation by the reset control unit 307 may be performed by, for example, comparing the voltage or the width of the voltage signal with a predetermined reference. For example, if the voltage of the voltage signal is compared with a predetermined voltage and is higher than the predetermined voltage, it is determined that the transmitted radiation is detected. In this case, the predetermined voltage is set to a value sufficiently higher than each reference voltage 306 for detecting light. As described above, the voltage obtained when the radiation enters directly indicates a value about ten times higher than that of the voltage obtained when the light enters. Therefore, for example, a value more than ten times higher than that of each reference voltage 306 for detecting light can be set to the predetermined voltage. If the width of the voltage signal is monitored and a time from the rise to the fall of the voltage signal becomes equal to or more than a predetermined time, it may be determined that the transmitted radiation is detected. These determinations of the voltage and the width of the voltage signal may be used in combination. Determination methods of the reset control unit 307 can be selected appropriately in accordance with a use condition of the radiation imaging apparatus 100 such as the energy band of radiation to be measured or a restriction on the arrangement of the circuit of the sensor panel 106.

Figure 5:
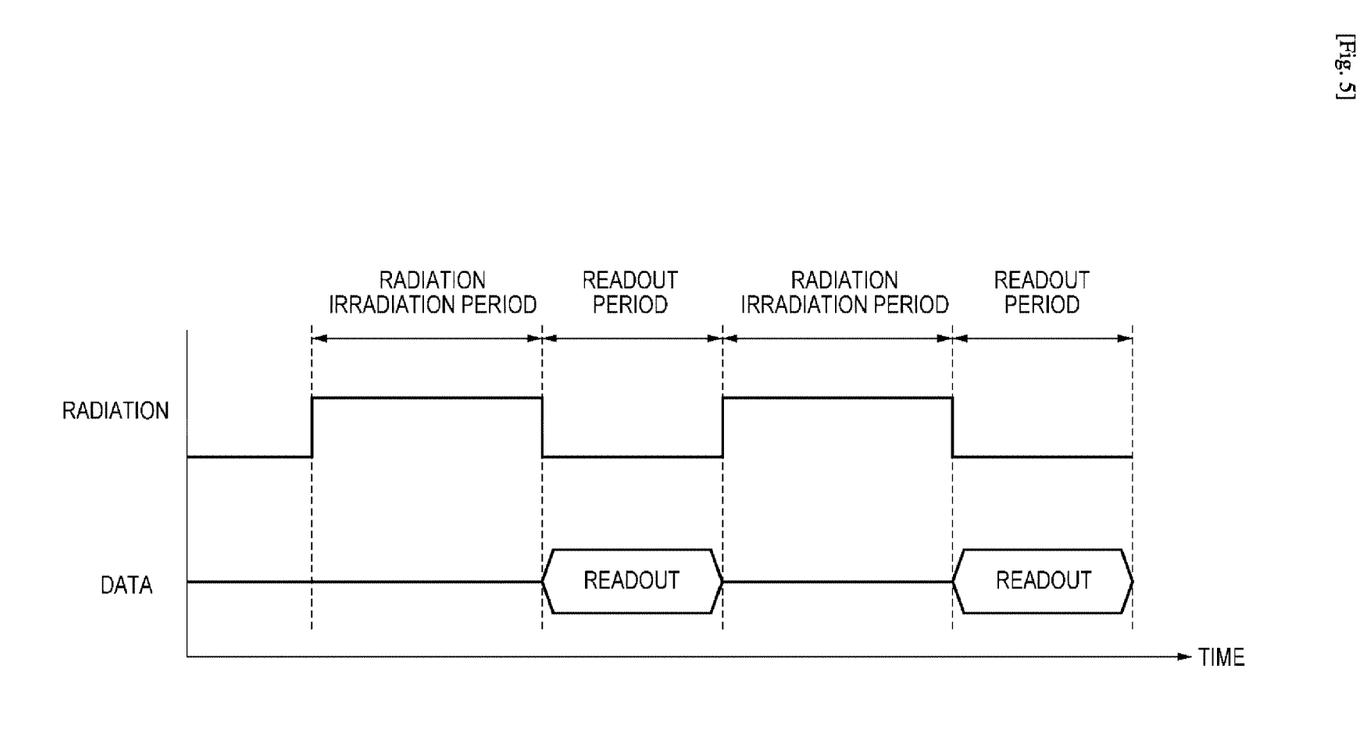
FIG. 5 is a timing chart showing an irradiation period and a readout period of the sensor panel of the radiation imaging apparatus in FIG. 1.

Driving of the radiation imaging system according to this embodiment will be described next. FIG. 5 is a timing chart showing the timing of driving the sensor panel 106 of the imaging unit 104. The waveforms in FIG. 5 represent the radiation irradiation period and the readout period of data DATA with respect to the abscissa representing the time. In FIG. 5, the radiation irradiation period is a period in which the object is irradiated with radiation by the irradiating unit 101, the radiation that has entered the sensor panel 106 is converted into light by the scintillator 105, and the detection count of light is obtained. The readout period is a period in which data DATA, which is the count obtained during the radiation irradiation period, is output from the sensor panel 106. As shown in FIG. 5, the sensor panel 106 can obtain a moving image by alternately performing the radiation irradiation period and the readout period. In addition, for example, a still image can be obtained by performing the radiation irradiation period and the readout period once.

Figure 6:
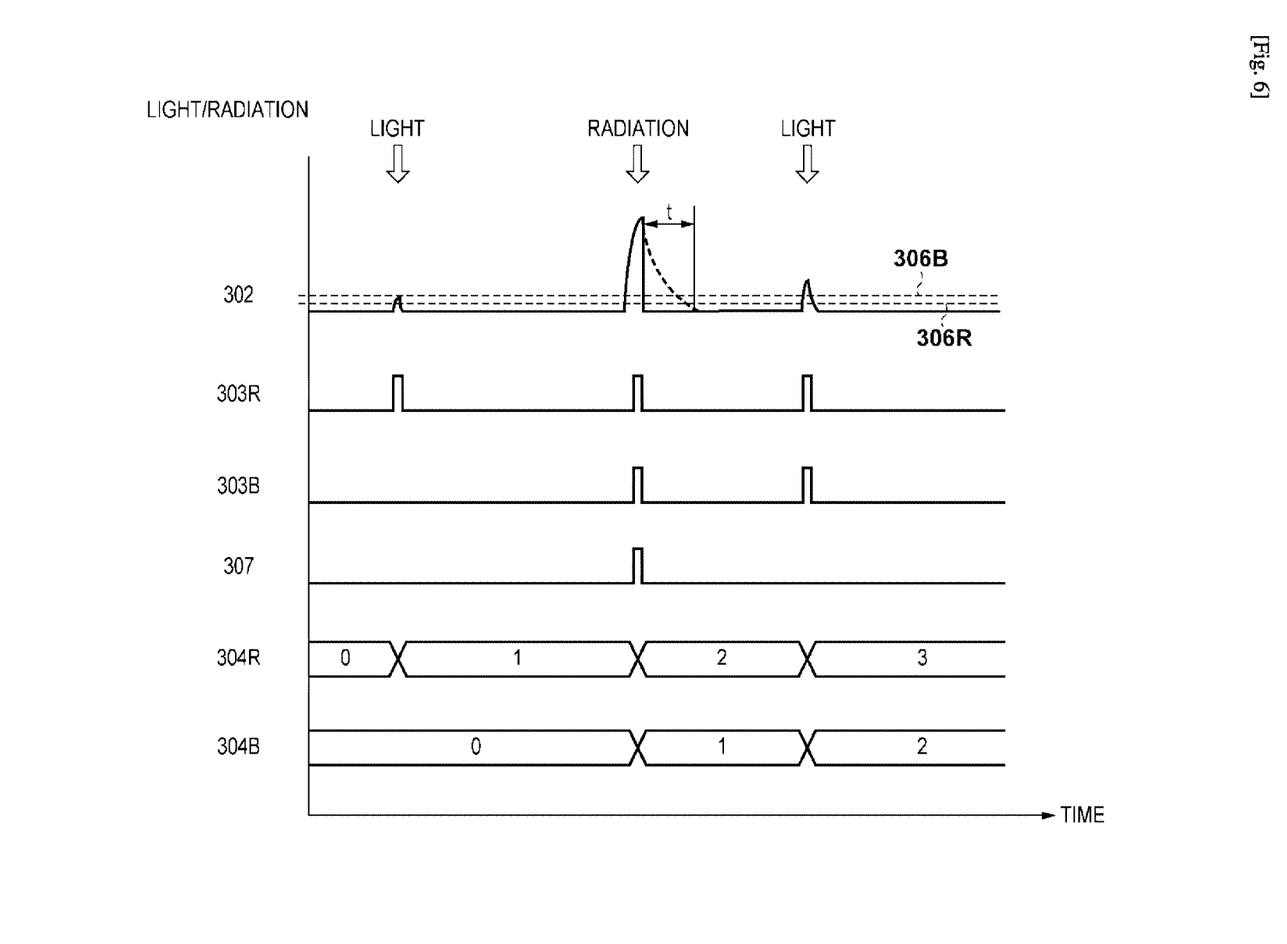
FIG. 6 is a timing chart showing an operation of each pixel in the irradiation period of the radiation imaging apparatus in FIG. 1.

The operation during the irradiation period in the pixel 201 arranged as shown in FIG. 3 will be described next with reference to FIG. 6. FIG. 6 is a timing chart showing the operation of each pixel 201 during the radiation irradiation period. The waveforms in FIG. 6 represent the output of the conversion unit 302, the outputs of the comparison units 303, and the number of times the digital value "1" is output from each comparison unit 303 stored in the corresponding count unit 304 and counted with respect to the abscissa representing the time. If the voltage of the voltage signal output from the conversion unit 302 is equal to or more than the reference voltage 306R, the digital value "1" is output, as the comparison result signal, from the comparison unit 303R, and the count unit 304R obtains the output count of the digital value "1" from the comparison unit 303R. If the voltage of the voltage signal output from the conversion unit 302 is equal to or more than the reference voltage 306B, the digital value "1" is output, as the comparison result signal, from each of the comparison units 303R and 303B, and the corresponding one of the count units 304R and 304B obtains the output count of the digital value "1". If radiation enters the light detector 301 directly, a voltage signal having a large amplitude is output, and the reset control unit 307 determines that the light detector 301 detects the transmitted radiation and outputs a signal for resetting the conversion unit 302. By the signal from the reset control unit 307, like the waveform shown in FIG. 6, the conversion unit 302 is reset and the voltage signal is reset.

Figure 7:
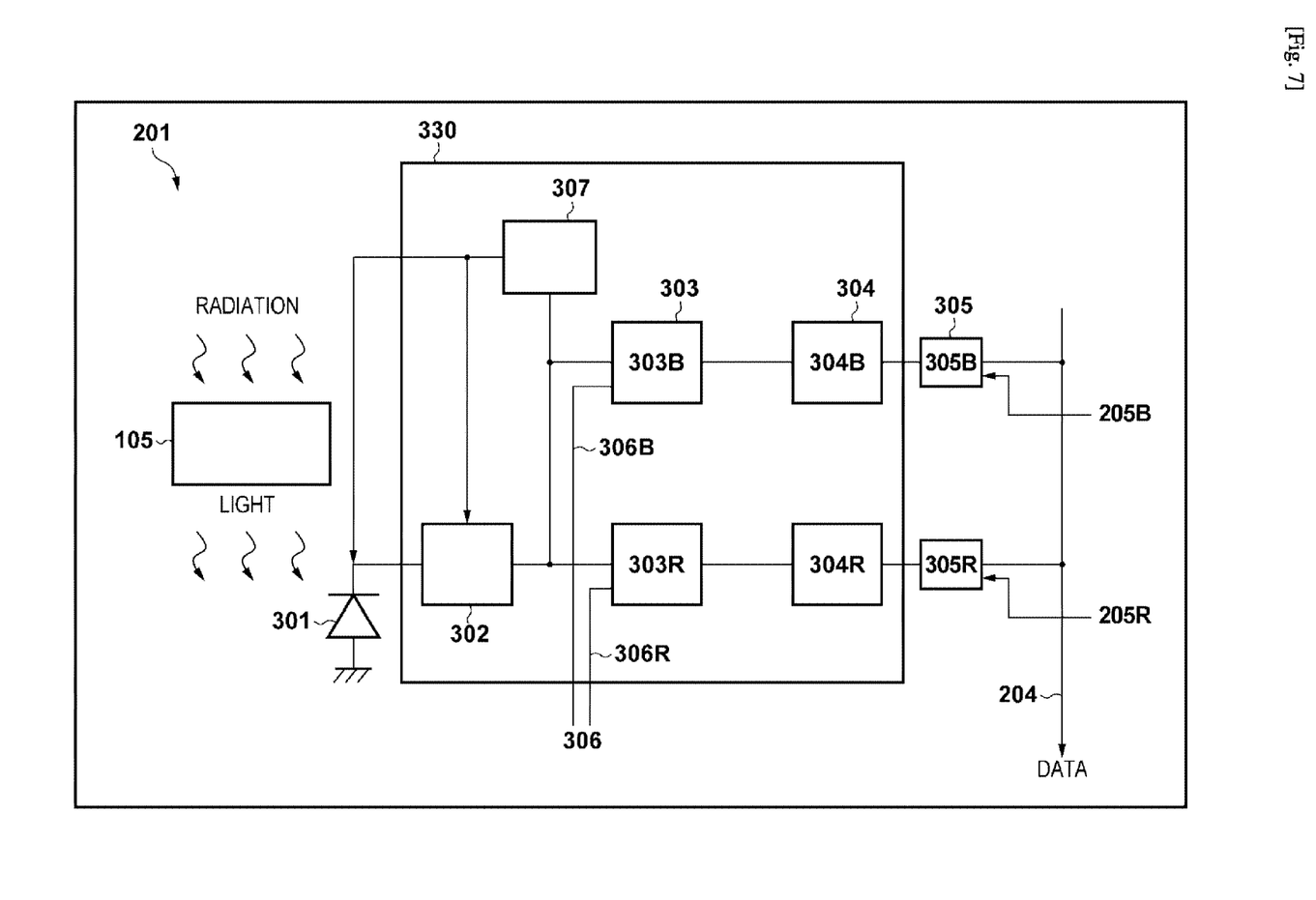
FIG. 7 is a block diagram showing a modification of the arrangement of the pixel in FIG. 3.

In this embodiment, the signal from the reset control unit 307 resets a component other than the conversion unit 302. FIG. 7 is a block diagram showing a modification of the arrangement of the pixel 201. As shown in FIG. 7, the output of the reset control unit 307 may be connected not only to the conversion unit 302 but also to the light detector 301. If it is determined that the light detector 301 detects radiation that has transmitted through the scintillator 105, the conversion unit 302 and the light detector 301 are reset simultaneously. For example, if radiation directly enters the light detector 301 using the photodiode or the like, the larger amount of charges is generated, and thus the light detector 301 is saturated more easily than in a case in which light enters. While the light detector 301 is saturated, even if light enters the light detector, it is impossible to detect the incident light. In the arrangement shown in FIG. 7, if the reset control unit 307 determines that the light detector 301 detects the transmitted radiation, it resets not only the conversion unit 302 but also the light detector 301 immediately. This makes it possible to restart detection of light immediately in the light detector 301.

Figure 8:
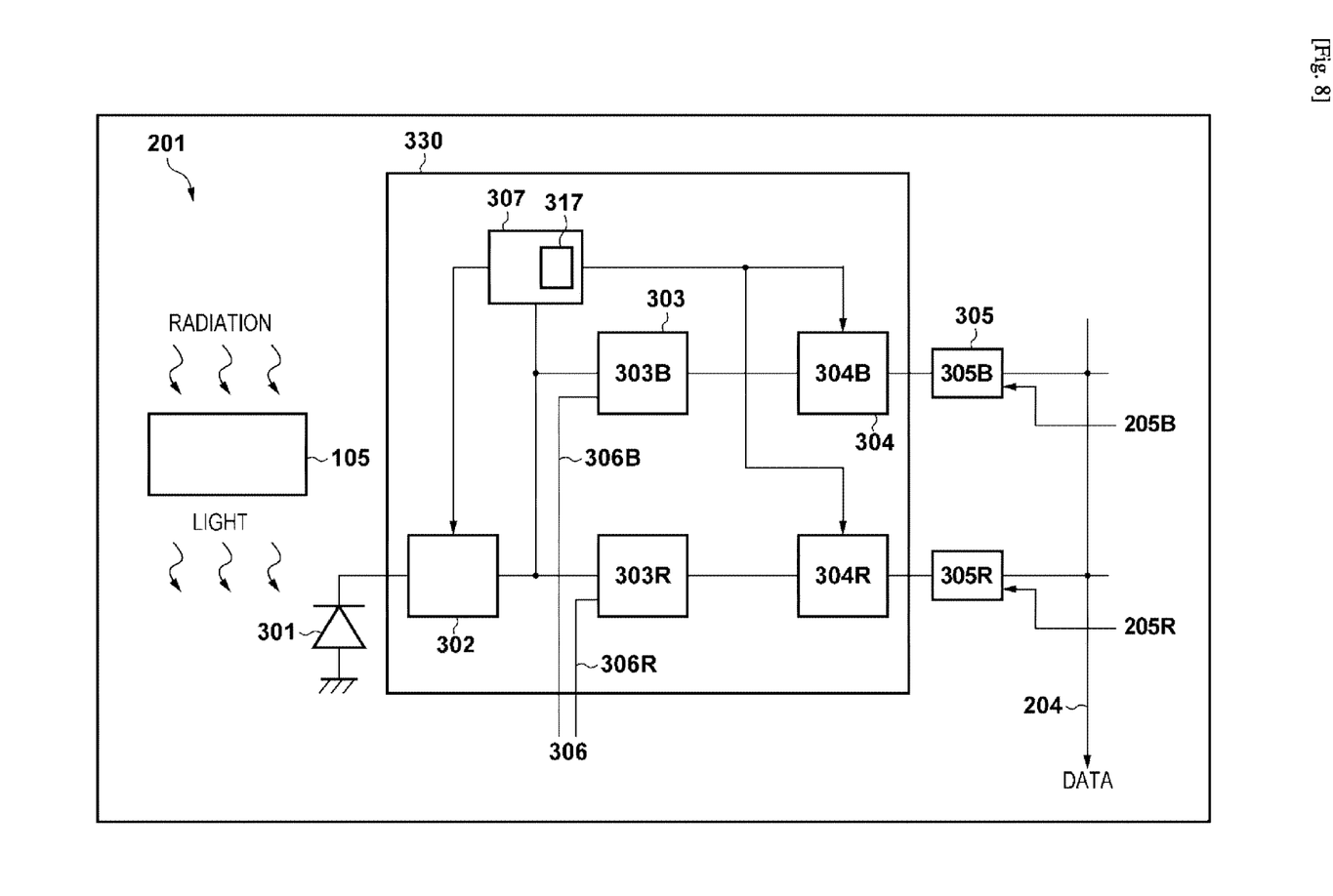
FIG. 8 is a block diagram showing a modification of the arrangement of the pixel in FIG. 3.

The signal from the reset control unit 307 is not limited to be used to reset the light detector 301 and the conversion unit 302. FIG. 8 shows a modification of the arrangement of the pixel 201. As shown in FIG. 8, the output of the reset control unit 307 may be connected to each count unit 304. If radiation that has transmitted through the scintillator 105 enters the light detector 301, a voltage signal output from the conversion unit 302 becomes about ten times larger, in amplitude, than a voltage signal output by detecting light. In this case, a voltage greatly exceeds each reference voltage 306 regardless of the energy of radiation that has entered the scintillator 105, and the digital value "1" is output from the corresponding one of the comparison units 303R and 303B as shown in FIG. 5. Each of the count units 304R and 304B obtains this count and increases the storage count by one. The count in this case is lower in reliability of energy determination than the count obtained when light converted by the scintillator 105 is detected. Consequently, this may lead to a reduction in image quality of a captured image. To cope with this, if the reset control unit 307 detects radiation and outputs a signal, each count unit may change the count of digital value "1" by the signal from the reset control unit 307. For example, in the arrangement shown in FIG. 8, if the reset control unit 307 detects the radiation and outputs the signal, it becomes possible to remove a count low in reliability by performing a process of subtracting, by one, counts of all the count units 304 in response to the input of this signal. For example, a memory unit 317 may also be installed in the reset control unit 307. The determined count that the light detector 301 detects radiation may be stored in the memory unit 317 in the reset control unit 307. Each count unit may subtract a count finally determined from the counts of all the count units 304 of the pixels 201.

Assume that the above-described operation during the irradiation period can be performed by setting the operating frequency of each pixel 201 and the irradiation amount of the irradiating unit 101 to be values that can count radiation photons one by one. For example, the operating frequency of each pixel 201 can be set in the range of 10 kHz to a few MHz (for example, about 100 kHz). Alternatively, the irradiation amount of the irradiating unit 101 can be set to a value obtained when the tube voltage is about 100 kV and the tube current is about 10 mA.

Figure 9:
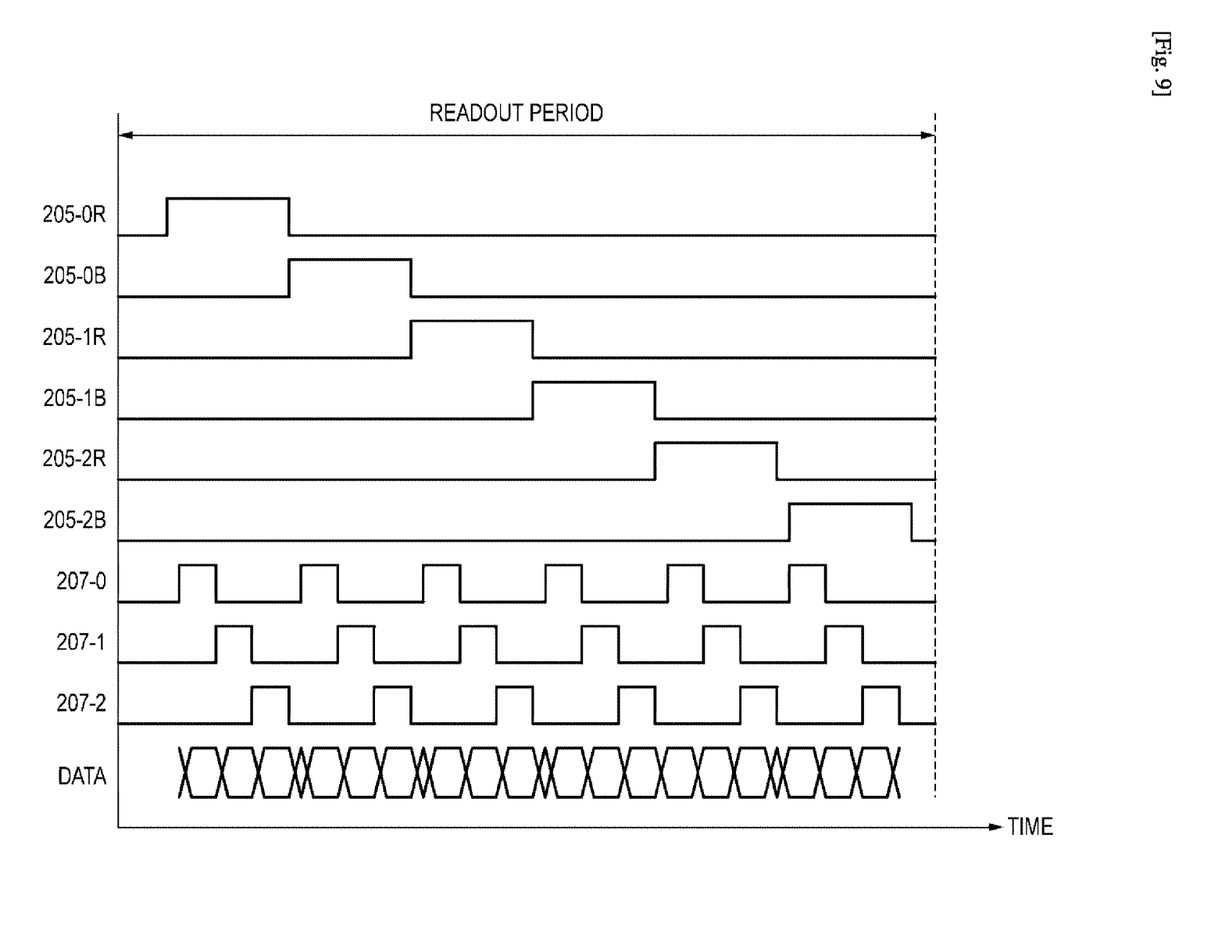
FIG. 9 is a timing chart showing an operation of each pixel in the readout period of the radiation imaging apparatus in FIG. 1.

The operation during the readout period of each pixel 201 arranged as shown in FIG. 3 will be described next with reference to FIG. 9. FIG. 9 is a timing chart showing the operation of each pixel 201 during the readout period. The waveforms in FIG. 9 represent the signal supply to each signal line 205, the signal supply to each signal line 207, and the output of data DATA obtained from each column selection circuit 208 with respect to the abscissa representing the time. As shown in FIG. 9, signals are sequentially supplied to the plurality of signal lines 205 and the plurality of signal lines 207. For example, when a signal supply operation to a signal line 205-0R is started, data indicating the output count of the comparison result signal of a level indicating a specific light intensity is supplied from the output unit 305R of each pixel 201 connected to the signal line 205-0R to a corresponding one of the column selection circuits 208. Then, during the signal supply period of the signal line 205-0R, signals are sequentially supplied to the plurality of signal lines 207, and data DATA are sequentially output from the plurality of column selection circuits 208 to the output line 206.

In this embodiment, the processor 103 obtains the captured image from the sensor panel 106, as shown in FIG. 1. This captured image is obtained by reading out the value of each count unit 304 arranged in each pixel 201 of the sensor panel 106 via the output line 206. The obtained captured image may be displayed without any change. However, the present invention is not limited to this, and arbitrary image processing may be performed. For example, image processing in which only the components of direct rays are used for image formation may be performed to remove scattered rays without using a grid. The energy spectrum of radiation may be estimated by performing arithmetic processing on the count value of each pixel 201. The direction and the distance of the irradiating unit 101 may be estimated from the count values of the plurality of pixels 201. Further, the composition and the physical property value of a substance may be calculated from the number of radiation photons of each energy that transmits through the object and a linear attenuation coefficient in each energy. For example, a process of calculating the effective atomic number of the object may be performed. For example, a process of correcting beam hardening may also be performed in which the relatively larger number of radiation photons having high energy enter as the object becomes thicker.

A radiation imaging apparatus (radiation imaging system) according to a second embodiment of the present invention will be described. Although the function of detecting pileup and the function of the reset control unit according to the aforementioned first embodiment use the processing unit 330 arranged in each pixel 201, these functions can be implemented by, for example, a program or software in the processor 103. That is, each pixel 201 can be formed by a circuit to output a signal corresponding to the light converted by the scintillator 105 and the detection count of the pileup and the output count of the comparison result signal can be obtained outside each pixel 201.

Figure 10:
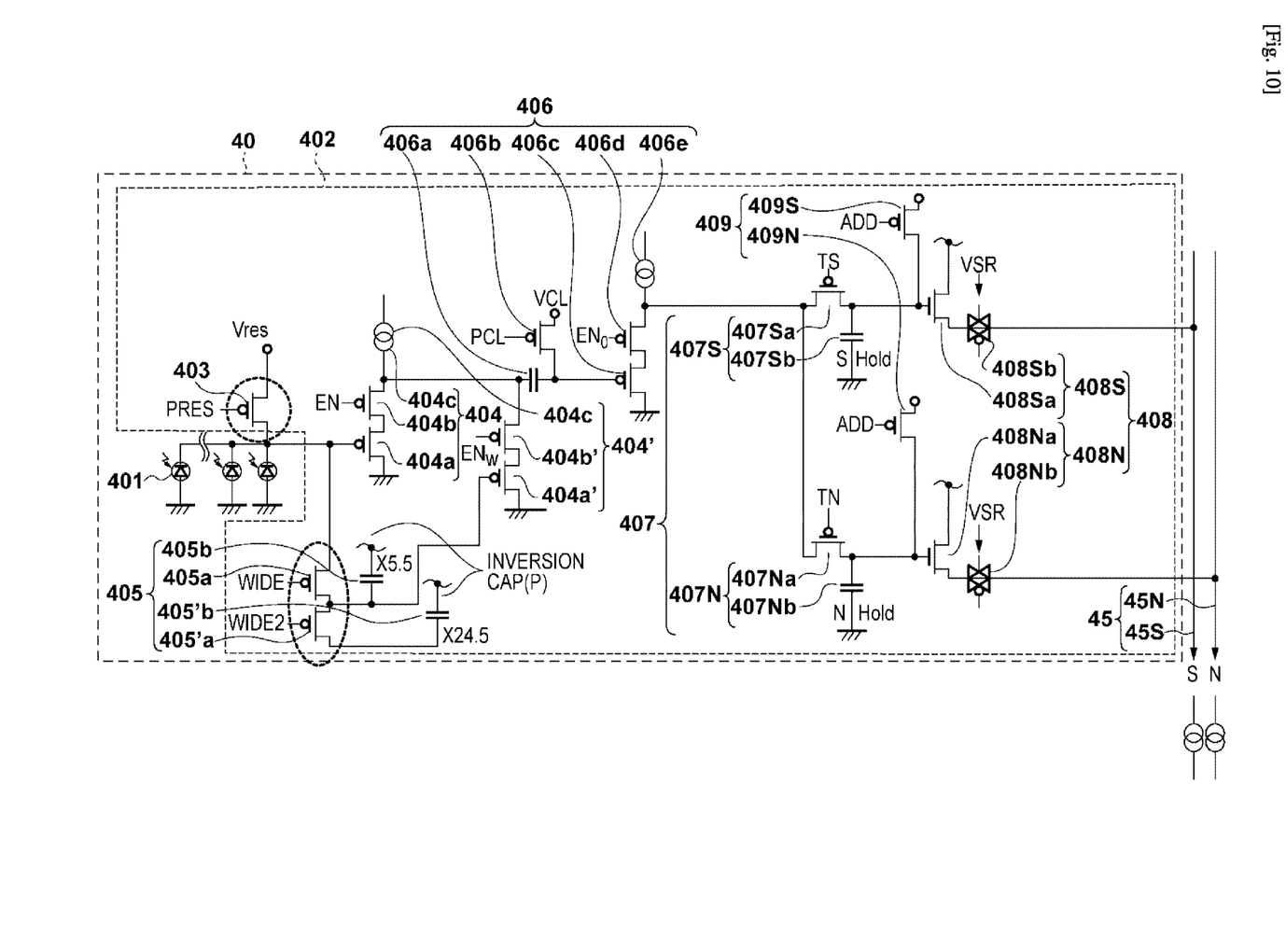
FIG. 10 is a view showing the arrangement of a pixel in a radiation imaging apparatus according to a second embodiment of the present invention.

FIG. 10 is a view showing an equivalent circuit of a pixel in a sensor panel 106 according to this embodiment. A pixel 40 in the sensor panel 106 of this embodiment can include photoelectric conversion elements 401 and an output circuit unit 402. The photoelectric conversion elements 401 can typically be photodiodes. The output circuit unit 402 can include an amplification circuit unit 404, a clamp circuit unit 405, a sample and hold circuit unit 407, and a selection circuit unit 408.

Each photoelectric conversion element 401 includes a charge accumulation portion connected to the gate of a MOS transistor 404a of the amplification circuit unit 404. The source of the MOS transistor 404a is connected to a current source 404c via a MOS transistor 404b. The MOS transistor 404a and the current source 404c form a source follower circuit. The MOS transistor 404b is an enable switch which is turned on to set the source follower circuit in an operation state when an enable signal EN supplied to its gate is set at an active level.

In an example shown in FIG. 10, the charge accumulation portion of each photoelectric conversion element 401 and the gate of the MOS transistor 404a form a common node, and this node functions as a charge-voltage conversion unit that converts charges accumulated in the charge accumulation portion into a voltage. That is, a voltage V (=Q/C) determined by charges Q accumulated in the charge accumulation portion and a capacitance value C of the charge-voltage conversion unit appears in the charge-voltage conversion unit. The charge-voltage conversion unit is connected to a reset potential Vres via a reset switch 403. When a reset signal PRES is set at the active level, the reset switch 403 is turned on, and the potential of the charge-voltage conversion unit is reset to the reset potential Vres.

A clamp circuit unit 406 clamps, using a clamp capacitor 406a, noise output by the amplification circuit unit 404 in accordance with the reset potential of the charge-voltage conversion unit. That is, the clamp circuit unit 406 is a circuit configured to cancel this noise from a signal output from the source follower circuit in accordance with charges generated by photoelectric conversion in each photoelectric conversion element 401. This noise can contain kTC noise at the time of reset. Clamping is performed by setting a clamp signal PCL at the active level to set a MOS transistor 406b in an ON state, and then setting the clamp signal PCL at an inactive level to set the MOS transistor 406b in an OFF state. The output side of the clamp capacitor 406a is connected to the gate of a MOS transistor 406c. The source of the MOS transistor 406c is connected to a current source 406e via a MOS transistor 406d. The MOS transistor 406c and the current source 406e form a source follower circuit. The MOS transistor 406d is an enable switch which is turned on to set the source follower circuit in the operation state when an enable signal EN0 supplied to its gate is set at the active level.

A signal output from the clamp circuit unit 406 in accordance with the charges generated by photoelectric conversion in each photoelectric conversion element 401 is written, as an optical signal, in a capacitor 407Sb via a switch 407Sa by setting an optical signal sampling signal TS at the active level. A signal output from the clamp circuit unit 406 when the MOS transistor 406b is set in the ON state immediately after the potential of the charge-voltage conversion unit is reset is a clamp voltage. This noise signal is written in a capacitor 407Nb via a switch 407Na by setting a noise sampling signal TN at the active level. This noise signal includes the offset component of the clamp circuit unit 406. The switch 407Sa and the capacitor 407Sb form a signal sample and hold circuit 407S. The switch 407Na and the capacitor 407Nb form a noise sample and hold circuit 407N. The sample and hold circuit unit 407 includes the signal sample and hold circuit 407S and the noise sample and hold circuit 407N.

When a driving circuit unit 41 drives a row selection signal VST at the active level, a signal (optical signal) held in the capacitor 407Sb is output to a signal line 45S via a MOS transistor 408Sa and a row selection switch 408Sb. At the same time, a signal (noise) held in the capacitor 407Nb is also output to a signal line 45N via a MOS transistor 408Na and a row selection switch 408Nb. The MOS transistor 408Sa forms a source follower circuit together with a constant current source (not shown) provided in the signal line 45S. Similarly, the MOS transistor 408Na forms a source follower circuit together with a constant current source (not shown) provided in the signal line 45N. The MOS transistor 408Sa and the row selection switch 408Sb form a signal selection circuit unit 408S. The MOS transistor 408Na and the row selection switch 408Nb form a noise selection circuit unit 408N. The selection circuit unit 408 includes the signal selection circuit unit 408S and the noise selection circuit unit 408N.

The pixel 40 may include an addition switch 409S that adds optical signals of the plurality of adjacent pixels 40. In an addition mode, an addition mode signal ADD is set at the active level, and the addition switch 409S is set in the ON state. Consequently, the addition switch 409S connects the capacitors 407Sb of the adjacent pixels with each other, averaging the optical signals. Similarly, the pixel 40 may include an addition switch 409N that adds noise of the plurality of adjacent pixels 40. When the addition switch 409N is set in the ON state, the addition switch 409N connects the capacitors 407Nb of the adjacent pixels with each other, averaging the noise. The addition unit 409 includes the addition switch 409S and the addition switch 409N.

The pixel 40 may include a sensitivity change unit 405 configured to change sensitivity. The pixel 40 can include, for example, a first sensitivity conversion switch 405$a$ and a second sensitivity conversion switch 405$a'$, and their accompanying circuit elements. When a first change signal WIDE is set at the active level, the first sensitivity conversion switch 405$a$ is turned on, and the capacitance value of a first additional capacitance 405$b$ is added to the capacitance value of the charge-voltage conversion unit. This decreases sensitivity of the pixel 40. When a second change signal WIDE2 is set at the active level, the second sensitivity conversion switch 405$a'$ is turned on, and the capacitance value of a second additional capacitance 405$b'$ is added to the capacitance value of the charge-voltage conversion unit. This further decreases sensitivity of the pixel 40. By adding a function of thus decreasing sensitivity of the pixel 40, it becomes possible to receive the larger amount of light and enlarge a dynamic range. When the first change signal WIDE is set at the active level, an enable signal ENw is set at the active level to cause a MOS transistor 404$a'$, instead of the MOS transistor 404$a$, to perform a source follower operation.

The output from such an above-described pixel circuit is converted into a digital value by an A/D converter (not shown), and then supplied to the processor 103. Then, processes corresponding to the operations of a conversion unit 302, comparison units 303, count units 304, and reset control unit 307 are performed by software in the processor 103.

First, the processor 103 calculates a differential value of the output of the pixel circuit as the process corresponding to each conversion unit 302. Next, the processor 103 compares the calculated differential value with a digital value corresponding to each reference voltage 306 as the process corresponding to the corresponding comparison unit 303. The processor 103 outputs a digital value "1" if the differential value is equal to or more than the digital value corresponding to each reference voltage 306 and outputs a digital value "0" if the differential value is less than the digital value corresponding to each reference voltage 306. Then, as the process corresponding to each count unit 304, the output count of the digital value "1" is obtained. Further, as the process corresponding to the reset control unit 307, if it is determined that a light detector 301 detects radiation from the differential circuit, for example, the light detector 301 is reset. At this time, as the process corresponding to each count unit 304, a count value may be changed. Then, the processor 103 generates an image based on the count. These processes can be executed, for example, by the CPU of the processor 103. The storage region that stores the detection count is allocated in the memory of the processor 103. There can be a plurality of digital values corresponding to the reference voltages 306 and functions that perform the processes corresponding to the comparison units 303 and the count units 304 in accordance with, for example, the levels of light intensity.

The functions of a processing unit 330 including the conversion unit 302, the comparison units 303, the count units 304, and the reset control unit 307 according to the present invention can be arranged in each pixel 201 of the sensor panel 106 as in the first embodiment. Alternatively, all the processes can be performed by software as in the second embodiment. However, the present invention is not limited to these embodiments. At least some of the processes, such as the conversion unit 302 and the comparison units 303, performed in the processing unit 330 can be arranged in each pixel 201 of the sensor panel 106 and the remaining processes corresponding to the count units 304 and the reset control unit 307 can be performed by software. Furthermore, the functions can be performed not by software but by a circuit provided outside the sensor panel 106. In this case, the circuit is formed preferably by, for example, FPGA.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-137225, filed Jul. 8, 2015, which is hereby incorporated by reference wherein in its entirety.

The invention claimed is:

1. A radiation imaging apparatus comprising:
a scintillator configured to convert radiation into light;
a sensor panel in which a plurality of pixels each comprising a light detector configured to detect the light is arranged; and
a processing unit,
wherein the processing unit comprises:
a conversion unit configured to output a detection signal in accordance with a signal generated in the light detector by the incident light and radiation that has transmitted through the scintillator without being converted into light; and
a reset control unit configured to determine that the light detector detects the transmitted radiation based on a magnitude of the detection signal and reset the conversion unit if the light detector is determined to detect the transmitted radiation.

2. The apparatus according to claim 1, wherein the reset control unit resets the light detector if the light detector is determined to detect the transmitted radiation.

3. The apparatus according to claim 1, wherein the radiation imaging apparatus generates a captured image based on an output count of the detection signal.

4. The apparatus according to claim 1, wherein the conversion unit comprises a voltage conversion unit configured to convert the signal generated in the light detector into a voltage signal and outputs the voltage signal as the detection signal.

5. The apparatus according to claim 4, wherein the voltage conversion unit comprises a differential circuit.

6. The apparatus according to claim 4, wherein the reset control unit determines that the light detector detects the transmitted radiation if a voltage of the voltage signal is higher than a predetermined voltage.

7. The apparatus according to claim 6, wherein in order to generate a captured image, the processing unit further comprises:
    a comparison unit configured to compare the voltage of the voltage signal with a reference voltage and output a comparison result signal if the voltage of the voltage signal is not lower than the reference voltage; and
    a count unit configured to store an output count of the comparison result signal, and
    wherein the predetermined voltage is not less than ten times higher than the reference voltage.

8. The apparatus according to claim 4, wherein the reset control unit determines that the light detector detects the transmitted radiation if a time from a rise to a fall of the voltage signal is longer than a predetermined time.

9. The apparatus according to claim 4, wherein in order to generate a captured image, the processing unit further comprises:
    a comparison unit configured to compare the voltage of the voltage signal with a reference voltage and output a comparison result signal if the voltage of the voltage signal is not lower than the reference voltage; and
    a count unit configured to store an output count of the comparison result signal.

10. The apparatus according to claim 9, wherein if the reset control unit determines that the light detector detects the transmitted radiation, the count unit changes the count.

11. The apparatus according to claim 10, wherein if the reset control unit determines that the transmitted radiation is detected, the count unit subtracts the count by one.

12. The apparatus according to claim 10, wherein the reset control unit further comprises a memory unit configured to store a determined count that the light detector detects the transmitted radiation, and
    the count unit subtracts the count in accordance with the determined count stored in the memory unit.

13. The apparatus according to claim 1, wherein at least a part of the processing unit is arranged in each pixel of the plurality of pixels.

14. A control method of a radiation imaging apparatus that comprises a scintillator configured to convert radiation into light and a sensor panel in which a plurality of pixels each comprising a light detector configured to detect the light is arranged, the method comprising:
    outputting a detection signal in accordance with a signal generated in the light detector by the incident light and radiation that has transmitted through the scintillator without being converted into light;
    determining that the light detector detects the transmitted radiation based on a comparison result between the detection signal and a predetermined reference; and
    resetting the detection signal if the light detector is determined to detect the transmitted radiation.

15. A non-transitory computer-readable medium storing, in executable form, a program for causing a computer to execute each step of a control method of a radiation imaging apparatus that comprises a scintillator configured to convert radiation into light and a sensor panel in which a plurality of pixels each comprising a light detector configured to detect the light is arranged, the method comprising:
    outputting a detection signal in accordance with a signal generated in the light detector by the incident light and radiation that has transmitted through the scintillator without being converted into light;
    determining that the light detector detects the transmitted radiation based on a comparison result between the detection signal and a predetermined reference; and
    resetting the detection signal if the light detector is determined to detect the transmitted radiation.

* * * * *